US00PP36309P2

(12) United States Plant Patent
Snijder

(10) Patent No.: US PP36,309 P2
(45) Date of Patent: Dec. 10, 2024

(54) ***PELARGONIUM* PLANT NAMED 'PEQZ0106'**

(50) Latin Name: ***Pelargonium* x *interspecific***
Varietal Denomination: PEQZ0106

(71) Applicant: SYNGENTA CROP PROTECTION AG, Basel (CH)

(72) Inventor: Ronald Christiaan Snijder, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/831,064

(22) Filed: May 25, 2024

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324, 326
See application file for complete search history.

*Primary Examiner* — Susan McCormick Ewoldt
*Assistant Examiner* — Zachariah Allan Kay
(74) *Attorney, Agent, or Firm* — Dale Skalla

(57) ABSTRACT

A new *Pelargonium* plant named PEQZ0106 particularly distinguished by white colored inflorescences with a large vivid rose spot in the middle of the floret, held above medium green foliage, on a mounding plant.

1 Drawing Sheet

Latin name of the genus and species of the plant claimed: *Pelargonium* x interspecific.

Varietal denomination: 'PEQZ0106'.

BACKGROUND OF THE NEW PLANT

The present invention comprises a new *Pelargonium*, botanically known as *Pelargonium* interspecific, and hereinafter referred to by the variety name 'PEQZ0106'.

'PEQZ0106' is a product of a planned breeding program. The new cultivar 'PEQZ0106' has white colored inflorescences with a large vivid rose spot in the middle of the floret, held above dark green foliage, on a mounding plant.

'PEQZ0106' originates from a hybridization in a controlled breeding program made in July 2018 in a greenhouse in Enkhuizen, The Netherlands. The female parent was an unpatented plant of *P.* x interspecific parentage identified as 'PEZBE5098-6V' with a more spreading habit and larger plant size when compared to 'PEQZ0106'.

The male parent of 'PEQZ0106' was an unpatented, proprietary plant of P. x interspecific parentage, identified as 'PEZBE5077-6V' with rose colored florets when compared to 'PEQZ0106'. The resultant seed was sown in January 2019.

'PEQZ0106' was selected as one flowering plant within the progeny of the stated cross in May 2019 in a greenhouse in Enkhuizen, The Netherlands.

The first act of asexual reproduction of 'PEQZ0106' was accomplished when vegetative stem cuttings were propagated from the initial selection in June 2019 in a greenhouse in Enkhuizen, The Netherlands.

BRIEF SUMMARY OF INVENTION

Horticultural examination of plants grown from cuttings of the plant initiated in March 2024 in Enkhuizen, The Netherlands and continuing thereafter, has demonstrated that the combination of characteristics as herein disclosed for 'PEQZ0106' are firmly fixed and are retained through successive generations of asexual reproduction.

'PEQZ0106' has not been observed under all possible environmental conditions. The phenotype may vary significantly with variations in environment such as temperature, light intensity, and day length.

A Plant Breeder's Right for this cultivar has not yet been applied for. 'PEQZ0106' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0106' with colors being as true as possible with an illustration of this type.

Figure 1:
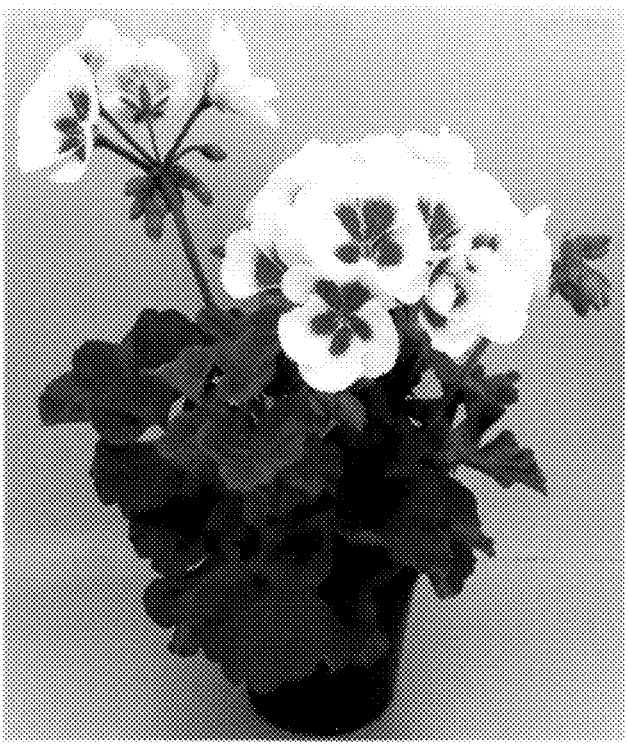
Figure 2:
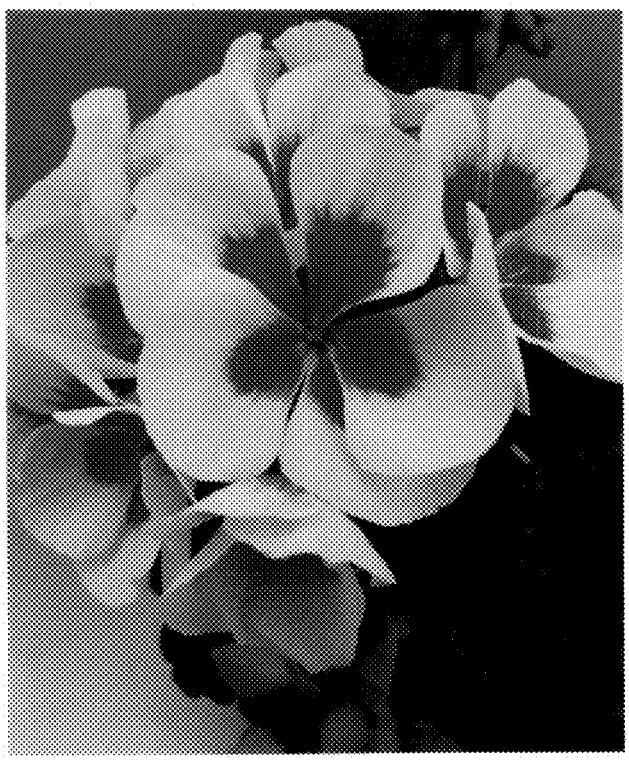

The photographic drawings show in FIG. 1, one flowering plants of the new variety and in FIG. 2, a close-up of an inflorescence.

DETAILED BOTANICAL DESCRIPTION

The plant descriptions and measurements were taken in Enkhuizen, The Netherlands in May 2024 under natural light. These plants were approximately 16 weeks old and were grown in a 12 cm pots, in a greenhouse trial. The plants shown in the photographs were about 16 weeks old growing in a 12 cm pot in a greenhouse. The photographs were taken in May 2023.

Color references are made to The Royal Horticultural Society Colour Chart (R.H.S.) of 2015.

TABLE 1

DIFFERENCES BETWEEN THE NEW VARIETY 'PEQZ0106' AND A MOST SIMILAR VARIETY

| | 'Tango White Splash' (not patented) | 'PEQZ0106' |
|---|---|---|
| Color upper surface of mature leaf: | Very dark green, RHS 139A | Dark green RHS 137B |
| Anthocyanin coloring of the peduncle: | Medium to strong | Medium |
| Plant habit: | Small size, very generative | Medium size, normal generative |

Plant:

*Form, growth and habit.*—Upright growth habit.
*Plant height.*—12-14 cm.
*Plant height (inflorescence included).*—22-25 cm.
*Plant width.*—24-27 cm.

Roots:

*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B but whiter.

Foliage:

*Variegation.*—Absent.
*Immature leaf, color upper surface.*—RHS 137A.
*Immature leaf, lower surface.*—RHS 147B.
*Mature leaf, color upper surface.*—RHS 137B.
*Mature leaf, color lower surface.*—RHS 147B.
*Length.*—6-8 cm.
*Width.*—8-10 cm.
*Shape.*—Cordate.
*Base shape.*—Cordate.
*Sinus of mature leaf.*—Wide.
*Leaf base openness.*—Variable, immature leaves wide open, mature leaves open.
*Apex shape.*—Acute.
*Margin.*—Slightly dentate.
*Texture upper side.*—Hirsute.
*Texture lower side.*—Hirsute.
*Leaf zonation color.*—None.
*Color of veins, upper surface.*—RHS 146B.
*Color of veins, lower surface.*—RHS 147C, distinct.
*Pattern of veining.*—Palmate.
*Petiole color.*—RHS 146B.
*Petiole length.*—4-10 cm.
*Diameter of petiole.*—0.2-0.4 cm.
*Texture.*—Pilose, hirsute, glandular hairs.

Stem:

*Quantity of branches.*—3-6.
*Color of stem.*—RHS 145B.
*Anthocyanin coloration of stem.*—Little to no anthocyanin coloration.
*Length of stem.*—9-20 cm.
*Diameter.*—0.5 cm.
*Length of internodes.*—1-4 cm.
*Texture.*—Sparsely hirsute, pilose, glandular hairs.

Peduncle:

*Color of peduncle.*—RHS 146A.
*Length of peduncle.*—13-16 cm.
*Peduncle diameter.*—0.3-0.5 cm.
*Texture.*—Hirsute, glandular hairs.
*Anthocyanin coloration of peduncle.*—Some to little anthocyanin coloration.

Pedicel:

*Color of pedicel.*—RHS 182A at the base fading to RHS 143C towards the apex.
*Length of pedicel.*—2-4 cm.
*Diameter of pedicel.*—0.15-0.2 cm.
*Texture.*—Sparsely pilose, glandular hairs.
*Pedicel swelling.*—Swelling was not observed.

Bud (just before opening):

*Color.*—RHS 159C.
*Length.*—1.5-2.0 cm.
*Width.*—0.6-0.8 cm.
*Shape.*—Elliptical.

Inflorescence:

*Type.*—Umbel; semi-spherical or nearly semi-spherical.
*Lastingness of individual flowers.*—7-9 days at 18° C. temperature.
*Number of inflorescences per plant.*—7-10, with 3-5 immature umbels in various stages.
*Average total number of buds.*—17.
*Fragrance.*—None.
*Umbel diameter.*—9-12 cm.
*Umbel depth.*—6-9 cm.

Corolla:

*Form.*—Single.
*Number of petals.*—5.
*Diameter of flower.*—5-6 cm.
*Depth of flower.*—1-2 cm.
*Side view shape.*—Concave.
*Color upper petals, upper surface.*—RHS 66A and RHS 155A.
*Color upper petals, lower surface.*—RHS 155A.
*Length of upper petals.*—2.5-3.1 cm.
*Width of upper petals.*—2.4-2.6 cm.
*Color lower petals, upper surface.*—RHS 66A and RHS 155B.
*Color lower petals, lower surface.*—RHS 155B.
*Markings on upper petals.*—Yes, distinct RHS 66A spot on lower half of upper petal.
*Markings on lower petals.*—Yes, distinct RHS 66A veins on lower half of lower petal.
*Length of lower petals.*—2.1-2.5 cm.
*Width of lower petals.*—2.0-2.2 cm.
*Petal shape.*—Obovate to spathulate.
*Apex shape.*—Rounded.
*Margin.*—Entire.
*Base.*—Attenuate.
*Petal texture.*—Papillose on both surfaces.

Calyx:

*Number of sepals.*—5.
*Color of sepals.*—RHS 60A fading to RHS 146B towards apex.
*Length of sepals.*—1.2-1.5 cm.
*Width of sepals.*—0.2-0.4 cm.
*Sepal shape.*—Lanceolate to linear.
*Apex shape.*—Acute.
*Margins.*—Mostly fused.
*Texture, upper surface.*—Glabrous.
*Lower surface.*—Glandular hairs, hirsute.
*Sepal flexing.*—Mostly unflexed sepals. The narrowest sepals might flex moderately.

Reproductive organs:

Gynoecium:

*Pistil*.—RHS 60C.

*Length*.—1.0 cm.

*Style color*.—RHS 60C.

*Style length*.—0.5 cm.

*Stigma color*.—RHS 65B.

*Ovary color*.—RHS 138C.

*Ovary length*.—0.5 cm.

*Ovary diameter*.—0.2 cm.

Androecium:

*Number of stamens*.—5 with 2 staminodes.

*Color of filaments*.—RHS 155B.

*Length filaments*.—0.4 cm.

*Anther color*.—RHS 179C.

*Length of anthers*.—0.2-0.4 cm.

*Color of pollen*.—RHS 171B.

*Pollen amount*.—Scarce.

*Fertility/seed set*.—Has not been determined to date.

*Disease/pest resistance*.—Has not been determined to date.

What is claimed is:

1. A new and distinct variety of *Pelargonium* plant named 'PEQZ0106' substantially as illustrated and described herein.

* * * * *